United States Patent [19]
Ogawa et al.

[11] Patent Number: 5,846,210
[45] Date of Patent: Dec. 8, 1998

[54] MEDICAL WIRE HAVING IMPLANTED DEVICE AND METHOD FOR USING THE SAME

[75] Inventors: Atsushi Ogawa, Kanagawa; Waro Taki, Osaka, both of Japan

[73] Assignee: Kaneka Medix Corporation, Osaka, Japan

[21] Appl. No.: 925,611

[22] Filed: Sep. 8, 1997

[30] Foreign Application Priority Data

Sep. 20, 1996 [JP] Japan .................................. 8-250576

[51] Int. Cl.⁶ .......................................................... A61B 5/00
[52] U.S. Cl. ............................................................ 600/585
[58] Field of Search .................................... 600/434, 585; 604/194; 606/32, 41, 195

[56] References Cited

U.S. PATENT DOCUMENTS

| | | |
|---|---|---|
| 4,346,712 | 8/1982 | Handa et al. . |
| 4,944,746 | 7/1990 | Iwata et al. . |
| 5,498,227 | 3/1996 | Mawad ........................................ 600/3 |

FOREIGN PATENT DOCUMENTS

| | | |
|---|---|---|
| 547530 | 6/1993 | European Pat. Off. . |
| 707830 | 4/1996 | European Pat. Off. . |
| 6-246004 | 9/1994 | Japan . |
| 7-265431 | 10/1995 | Japan . |
| 7-284534 | 10/1995 | Japan . |
| WO 91/13592 | 4/1991 | WIPO . |
| WO 94/06503 | 3/1994 | WIPO . |
| WO 95/12367 | 5/1995 | WIPO . |

*Primary Examiner*—Max Hindenburg
*Attorney, Agent, or Firm*—Frishauf, Holtz, Goodman, Langer & Chick P.C.

[57] ABSTRACT

A medical wire includes a conductive guide wire and an implanted device, which are connected to each other through a joint member. The joint member is heated by applying a high-frequency current through the guide wire, whereby the joint member is melted and severed so as to detach the implanted device from the guide wire. The joint member is composed of a rod of a swelling resin, the outer diameter of which increases by at least 10% when brought into contact with water. The medical wire may be inserted into a patient's body through a catheter arranged in the patient's body, during which an impedance reducing phenomenon that occurs between the guide wire and a counter electrode provided on the patient's body is detected, thereby confirming that the implanted device has been deposited properly in the patient's body.

11 Claims, 3 Drawing Sheets

MEDICAL WIRE HAVING IMPLANTED DEVICE AND METHOD FOR USING THE SAME

BACKGROUND OF THE INVENTION

1) Field of the Invention

The present invention relates to a medical wire to be used to deposit a desired implanted device at an intended site in a patient's body through a tubular organ thereof and to a method for using the same.

2) Description of the Background Art

Various problems are generally presented in treatment involving surgery to a patient's body. For example, the patient undergoing an operation must withstand the long hours of stress of the procedure. The surgeon, as well, is forced to endure intense concentration for the long period of operation. The danger of infection is always a possibility.

In order to lighten such stress and to perform a necessary operation safely and easily, various medical instruments such as catheters, guide wires and embolizing materials for occluding tubular organs such as vessels have recently been developed and been put to practical use.

With the recent advancement of medical instruments such as catheters and guide wires, for example, an endovascular operation in which the intended diseased part is approached through a vessel is currently often performed in the treatment of diseases such as arteriovenous malformation, cerebral aneurysm and carotid-cavernous fistula.

At present time, releasable balloons, coils, liquid embolizing substances, particulate embolizing substances and the like are used as tubular organ embolizing materials. Once such a embolizing material is left or released at erroneous or undesirable site in a tubular organ, however, it is generally next to impossible to recover or to change the site.

Under such circumstances, proposals have heretofore been made for releasable embolizing materials, by which an embolizing material can be pulled back and reinserted even when one fails to deposit it at the intended site, and can be released and left after confirmation of the disposed site.

For example, Japanese Patent Application (KOHYO) No. 500322/1993 (through PCT route) proposed a method for leaving a thrombus-forming member in an aneurysm, wherein the thrombus-forming member is provided at a distal end of a guide wire with a joint member made of a stainless steel, the thrombus-forming member is disposed at an intended site, and a positive current is applied to the guide wire to form a thrombus around the thrombus-forming member, and at the same time, to electrolyze the joint member, thereby severing the joint member to cause the thrombus-forming member to detach from the guide wire.

Japanese Patent Application (KOHYO) No. 501015/1995 (through PCT route) also discloses a means for detaching a thrombus-forming member by electrolyzing a joint member made of stainless steel.

However, these methods present the problem that fragments of the joint member as well as iron ions and nickel ions are formed by the electrolysis of the joint member made of stainless steel and released in the patient's body.

Furthermore, from a practical viewpoint, the method is problematic because it takes several minutes or longer to electrolyze one joint member of stainless steel to make it sever. Moreover, when several thrombus-forming members are inserted in the same aneurysm, the time required to detach the thrombus-forming members is further lengthened because the total surface area of conductive parts inevitably increases. In some cases, it may take 15 to 30 minutes or longer to electrolyze them.

If it takes a long time to detach the implanted devices as described above, the operation is lengthened, which imposes a great burden on the patient and the operating doctor.

On the other hand, Japanese Patent Application Laid-Open Nos. 246004/1994 and 284534/1995 describe a construction that an implanted device is connected to a guide wire through a joint member made of a shape-memory alloy, and the shape of the joint member is restored by heating to release the connection state. In addition, Japanese Patent Application (KOHYO) No. 502674/1995 (through PCT route), etc. also disclose a construction that an implanted device is connected to a guide wire through a mechanically releasable joint structure.

In the medical wires according to these techniques, however, the structure of the joint member used to detachably connect the implanted device to the guide wire is complicated, and so its production is much difficult. In addition, the joint member is low in reliability upon operation, and there is a possibility that the connection state of the joint member may be released, for example, during the inserting operation with the guide wire, or the implanted device may not be surely detached.

Japanese Patent Application Laid-Open No. 265431/1995 proposed a medical wire comprising a conductive guide wire and an implanted device connected to the guide wire with a joint member which is heated by applying a high-frequency current, thereby melting and severing the joint member, wherein the implanted device can be separated from the guide wire by applying a high-frequency current between the guide wire and a counter electrode provided on a patient's body.

This medical wire has merits that the connection structure between the guide wire and the implanted device is simple, and so the medical wire can be produced with relative ease, and that separating operation is also much easy, and so it takes a short time to detach the implanted device.

In such a medical wire, however, it is difficult to provide sufficiently great joint strength when a joint member having good fusibility is used. For example, there is a possibility that since its tensile strength is too low, the implanted device may not be reliably pulled back. When the outer diameter of the joint member is made so great that sufficient joint strength can be provided, the resulting medical wire involves a problem that it is difficult to provide good fusibility for the joint member.

In this medical wire, pushing force applied to the guide wire may not be normally transmitted to the implanted device when the guide wire is pushed to insert the implanted device into a catheter because of a change in connection state between the joint member and the guide wire or the implanted device or of flexing of the joint member, so that the pose of the implanted device may become an improper state. For example, the joint member is bent in an S shape, so that the implanted device to be situated in series in front of the guide wire may possibly be located in parallel with the distal part of the guide wire. When the connection state by the joint member is changed as described above, it is naturally next to impossible to deposit the implanted device at the intended site.

Such a medical wire is generally inserted through a catheter properly arranged in advance in a patient's body. The melting and severing operation of the joint member must be conducted at the time the whole of the implanted device has been pushed out of the distal opening of the catheter and deposited properly at the intended site, namely, at the time, in the case of an embolization treatment of, for example, a cerebral aneurysm, a state that the implanted device is completely deposited within the cerebral aneurysm, and the guide wire is scarcely projected from the catheter has been achieved.

As a method for confirming that such a proper deposition state has been achieved, there has been developed a method in which the insertion of a guide wire is conducted in a state that high-frequency voltage for measurement or detection is applied between the conductive guide wire and a counter electrode for body earth provided on the skin surface of the patient's body, and a phenomenon that an impedance between the guide wire and the counter electrode is maintained high while the distal end of the guide wire stays within the catheter, but the impedance greatly reduces at the time the whole of the implanted device has been pushed out of the catheter, so that the distal end of the guide wire has come into contact with humor within the patient's body at the distal opening of the catheter (this phenomenon is referred to as "impedance reducing phenomenon" in the present specification) is detected, thereby confirming that the implanted device has been deposited properly. In the present specification, this method is referred to as "impedance reduction detecting method".

In the case where such an impedance reduction detecting method is applied, however, the conductive implanted device may possibly come into direct contact with the distal end of the guide wire within the catheter, though the distal end of the guide wire has not been advanced to the distal opening of the catheter. In such a case, the impedance reducing phenomenon occurs when the distal end of the implanted device is discharged out of the distal opening of the catheter, so that the wrong deposited state of the implanted device may possibly be detected.

As described above, the conventional medical wire so constructed that the implanted device is separated from the guide wire by melting and severing the joint member with a high-frequency current involves problems that it is impossible to achieve good fusibility while obtaining sufficiently great joint strength between the joint member and the guide wire or the implanted device and that since the medical wire is often hardly inserted while maintaining it in a proper connection state, the implanted device may possibly not be deposited precisely at the intended site within the patient's body.

When the properly deposited state of the implanted device is detected by using the impedance reduction detecting method utilizing the impedance reducing phenomenon, there is a possibility that the detection of the properly deposited state may not be performed with high reliability.

SUMMARY OF THE INVENTION

It is therefore an object of the present invention to solve the above problems and to provide a medical wire in which an implanted device is separated from a guide wire by applying a high-frequency current to a joint member to melt and sever it, the implanted device can be connected to the guide wire with sufficiently great joint strength through the joint member having good fusibility, so that the medical wire can be inserted while maintaining a proper connection state, thereby surely depositing the implanted device at the intended site within a patient's body.

Another object of the present invention is to provide a method of detecting with high reliability a state that the implanted device is deposited properly at the intended site within a patient's body, upon using a medical wire in which an implanted device is separated from a guide wire by applying a high-frequency current to a joint member to melt and sever it.

The above objects can be achieved by the present invention described below.

According to the present invention, there is thus provided a medical wire having an implanted device, in which the implanted device is connected to a distal end of a conductive guide wire through a joint member, and the joint member is heated by applying a high-frequency current through the guide wire, whereby the joint member is melted and severed so as to detach the implanted device from the guide wire, wherein the joint member is composed of a rod of a swelling resin, the outer diameter of which increases by at least 10% when brought into contact with water.

The joint member may preferably be connected to the guide wire by inserting its proximal part into a coiled distal part of the guide wire and connected to the implanted device by inserting its distal part into a coil portion forming the implanted device.

In the above construction, the outer diameter of the joint member in a swollen state is preferably greater than any of the outer diameters of the coiled distal part of the guide wire and the coil portion forming the implanted device.

The joint member may preferably have an outer diameter of 0.10 to 0.35 mm in an unswollen state and of 0.25 to 1.00 mm in a swollen state, and a breaking strength of at least 100 g in a swollen state. The joint member may preferably be made of poly(vinyl alcohol) or a vinyl alcohol copolymer.

The clearance between the distal end of the guide wire and the proximal end of the implanted device connected through the joint member to the guide wire, may preferably be 0.3 to 5.0 mm.

The joint member may preferably be melted and severed by applying a high-frequency current of a frequency of 100 to 5,000 kHz and power of 0.1 to 20 W between the guide wire and a counter electrode.

According to the present invention, there is also provided a method for using the medical wire described above through a catheter arranged in a patient's body, which comprises dipping the joint member in a saline solution before insertion into the patient's body.

According to the present invention, there is further provided a method for using the medical wire described above through a catheter arranged in a patient's body, which comprises inserting the guide wire into the catheter in a state that high-frequency voltage for measurement is applied between the guide wire and a counter electrode provided on the patient's body, and detecting an impedance reducing phenomenon that an impedance between the guide wire and the counter electrode reduces rapidly, thereby confirming that the implanted device has been deposited properly in the patient's body.

The medical wire having such a construction as described above is inserted into the patient's body with or without using, for example, a catheter, whereby the implanted device is deposited properly at the intended site. In this state, a monopolar high-frequency current is applied to the joint member through the guide wire utilizing the conductivity of the guide wire, thereby heating the joint member so as to melt and sever it. As a result, the implanted device is separated from the guide wire to be left in the patient's body.

Since the joint member through which the implanted device is connected to the guide wire is composed of a rod of a resin having specific swelling characteristics, the joint strength of the joint member with the guide wire and the implanted device can be made sufficiently great utilizing the swelling of the joint member to increase its outer diameter by absorbing water upon bring the joint member into contact with, for example, physiological saline before insertion into the patient's body, or upon coming into contact with blood or other humors in the course of insertion into the patient's body. In particular, when joints of the guide wire and implanted device with the joint member are in the form of a coil, sufficiently great joint strength can be surely obtained by inserting both end parts of the joint member into the respective coil parts or portions to connect them.

Since the outer diameter of the joint member increases by swelling, the joint member undergoes neither bending nor deformation, and moreover the pushing force applied to the guide wire can be reliably transmitted to the implanted device through the joint member.

As a result, the medical wire can be inserted while maintaining a proper pose without changing the connection state of the implanted device with the guide wire through the joint member. Therefore, the implanted device can be reliably deposited at the intended site in the patient's body and also pulled back surely.

In addition, the joint member of the medical wire implemented for the patient's body contains a moderate amount of water by swelling, and hence can be successfully melted and severed by applying a high-frequency current.

Furthermore, since the outer diameter of the joint member increases by swelling and both of the guide wire and the implanted device can be reliably prevented from coming into direct contact with each other during use, the electrical insulation between them can be suitably ensured, and the implanted device can be reliably detached from the guide wire by applying a high-frequency current to the joint member.

According to the method of the present invention, in the use of such a medical wire as described above, direct contact of the implanted device with the guide wire, which causes an incorrect detection, can be prevented by the swollen joint member. Therefore, the state that the implanted device is deposited properly in a patient's body can be detected with high reliability by the impedance reduction detecting method.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described in detail according to the embodiments of the present invention with reference to the drawings.

Figure 1:
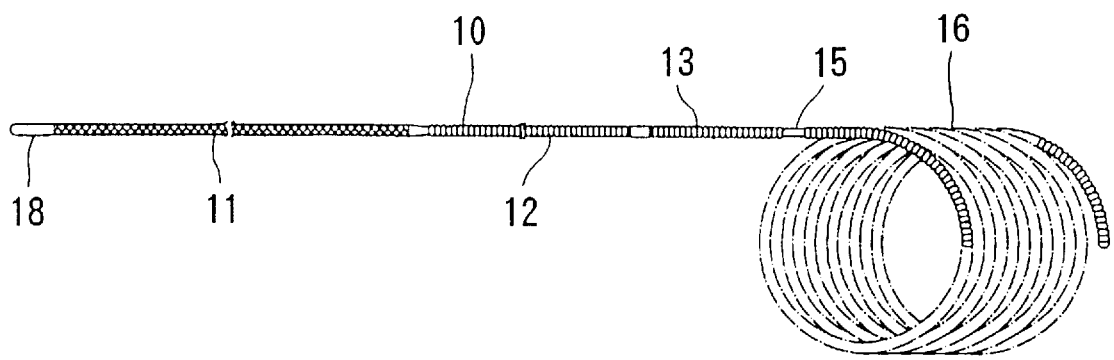
FIG. 1 illustrates a construction of a medical wire having an implanted device which is an embodiment of the present invention.

FIG. 1 illustrates the construction of a medical wire which is an embodiment of the present invention. The medical wire in this embodiment basically comprises a conductive guide wire 10 made of a metal, a joint member 15 in the form of a short rod, which is connected at its proximal end to a distal end of the guide wire 10, and an implanted device 16 connected to the distal end of the joint member 15.

The illustrated guide wire 10 comprises a proximal part 11 with a lubricating coating, a flexible part 12 adjacent thereto, and a distal X-ray impervious part 13 connected to the flexible part 12. The joint member 15 is connected to an end of the X-ray impervious part 13. The flexible part 12 and distal X-ray impervious part 13 of the guide wire 10 are constructed by, for example, closely winding a wire 0.01 to 0.2 mm in diameter at a pitch equal to its diameter on the peripheral surface of a core wire 0.03 to 2.0 mm in diameter to form a coil element of single, double or triple coil layers, for example. The guide wire 10 constructed by closely winding the wire on the peripheral surface of the core wire in a coiled form as described above is preferred since it combines sufficient flexibility with stiffness required for its insertion though it has a thin outer diameter.

A wire of conductive metallic material such as stainless steel may be used for the guide wire 10. An X-ray impervious wire composed of a metal such as platinum, silver or tungsten may be used in the distal X-ray impervious part 13.

The length of the guide wire 10 varies according to the intended application and could be 0.1 to 1.8 m, for example.

The surface lubricating coating in the proximal part 11 of the guide wire 10 may be formed by any suitable material. It may be generally provided by covering with one of various resins, for example, a fluorocarbon resin or hydrophilic resin.

The proximal part 11 is so constructed that at the most proximal end thereof, the wire is exposed to form a terminal part 18 through which a high-frequency current can be applied via suitable conductive members such as an electrical connector, plug and/or clip. For example, about 1 to 3 cm will suffice for the length of this terminal part 18.

The joint member 15 is melted and severed by heating with a high-frequency current, thereby detaching the implanted device 16 from the guide wire 10. The joint member 15 is composed of a rod of a swelling resin, which does not adversely affect the patient's body, and the outer diameter of which increases by at least 10% when brought into contact with water. Specifically, poly(vinyl alcohol) or a vinyl alcohol copolymer having a polymerization degree of 500 to 4,000, preferably 1,500 to 2,500 is preferably used as such a swelling resin.

Figure 2:
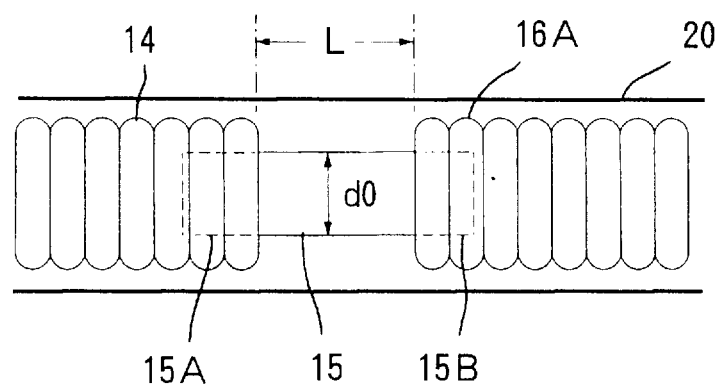
FIG. 2 illustrates a connection state with a joint member in the medical wire of FIG. 1 together with a catheter.

As illustrated in FIG. 2, the joint member 15 is fixedly connected to the guide wire 10 by further applying an adhesive in a state that its proximal part 15A has been inserted into the coiled distal part 14 of the guide wire 10.

An example of the implanted device 16 used in the present invention includes a coil piece used as a thrombus-forming member as illustrated in FIG. 1. In the present invention, for example, a double-coiled wire formed of a flexible material which is pliable, specifically, for example, a platinum alloy, should preferably be used in such a coil piece. The implanted device 16 formed of such a coil piece may carry or hold suitable substances.

As illustrated in FIG. 2, the implanted device 16 composed of a coil piece is fixedly connected to the joint member 15 by inserting the distal part 15B of the joint member 15 into the primary coil portion 16A of the implanted device 16 and further applying an adhesive thereto.

Figure 3:
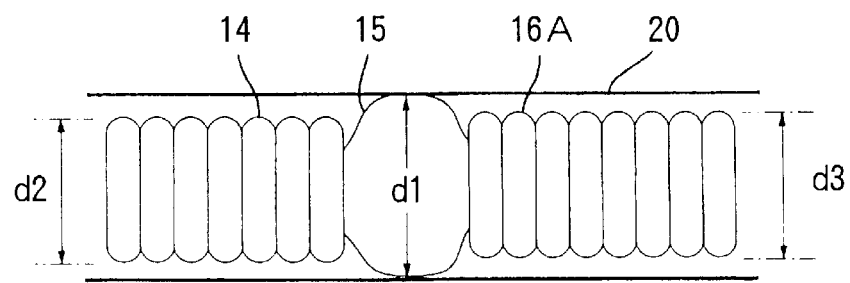
FIG. 3 illustrates a swollen state of the joint member as shown in FIG. 2.

The joint member 15 is composed of a rod of a swelling resin, the outer diameter of which increases by at least 10% when brought into contact with water. It is preferable that, as illustrated in FIG. 3, the outer diameter d1 of the joint member 15 in a swollen state is greater than any of the outer diameter d2 of the coiled distal part 14 of the guide wire 10 and the outer diameter d3 of the primary coil portion 16A of the implanted device 16.

It is also preferable that the joint member 15 should have an outer diameter d0 of 0.10 to 0.35 mm in an unswollen state and an outer diameter d1 of 0.25 to 1.00 mm in a swollen state by bringing it into contact with water, and in particular, its breaking strength in the swollen state be at least 100 g. The length of the joint member is 2 to 15 mm, preferably 5 to 10 mm. If a joint member having breaking strength in the swollen state smaller than 100 g is used, the joint member itself may possibly be broken in a pull-back operation.

On the other hand, the outer diameter d2 of the coiled distal part 14 of the guide wire 10 is preferably 0.1 to 2.0 mm.

A double-coiled wire which is produced by winding, for example, a wire having a diameter of 0.07 mm to form a primary coil having a diameter d3 of 0.1 to 1.0 mm and coiling the primary coil to form a secondary coil having a diameter of 2 to 40 mm, may preferably be used as the implanted device 16.

Figure 4:
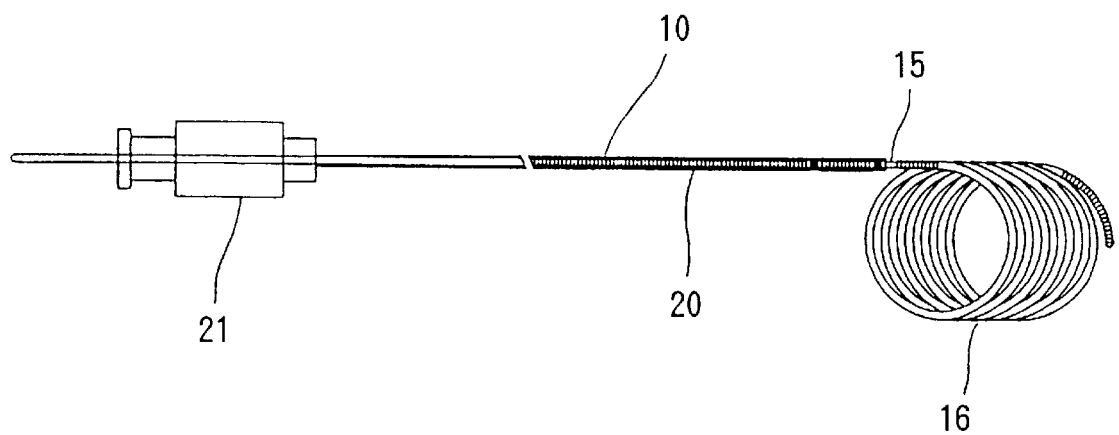
FIG. 4 illustrates an example of a specific means for implementing the medical wire of FIG. 1.
Figure 5:
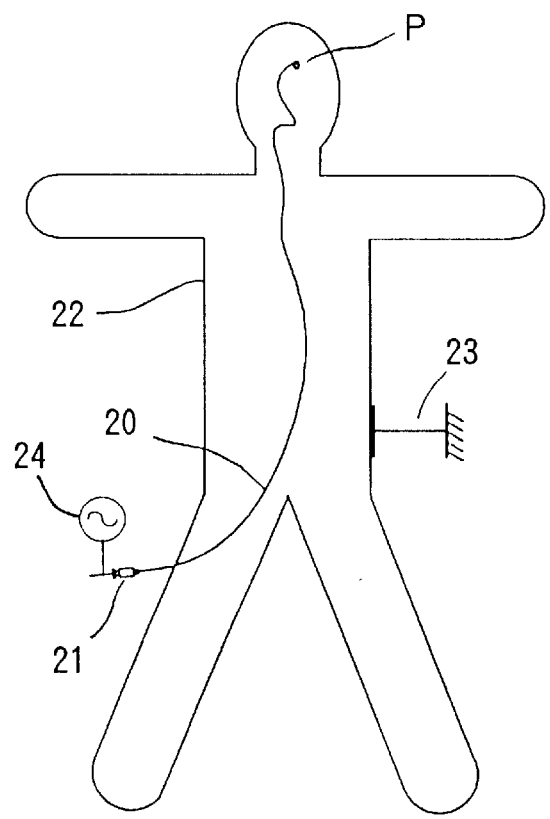
FIG. 5 schematically illustrates an instance where the medical wire according to the present invention is implemented for a cerebral aneurysm.

As illustrated in FIG. 4, the medical wire of the above-described construction is inserted into a patient's body to be treated by means of a suitable catheter 20. Specifically, the catheter 20 is inserted in the patient's body 22 by a conventional method as illustrated in FIG. 5, so that the distal end thereof is situated at the intended site at which the implanted device 16 is to be deposited, or the site P of a cerebral aneurysm in the illustrated embodiment. Reference numeral 21 indicates the proximal operating part of the catheter 20. For this catheter 20, an ordinary catheter, for example, a microcatheter can be used.

No limitation is imposed on the catheter 20 used herein so long as it has an inner diameter greater than the outer diameter d2 of the guide wire 10 and the outer diameter d3 of the implanted device 16. A catheter having an inner diameter smaller than the outer diameter d1 of the joint member 15 swollen may also be used because the joint member 15 in a swollen state becomes somewhat pliable and deformable locally.

In this stage, the medical wire is inserted into the catheter 20 through the proximal operating part 21 with the implanted device 16 in the lead. Then, the coil piece forming the implanted device 16 moves along within the catheter 20 as a single coil with the secondary coil thereof stretched in an essentially straight line along the catheter 20.

This inserting operation may be conducted under application of high-frequency voltage for measurement or detection between the guide wire 10 and a counter electrode 23 (see FIG. 5) for body earth provided on the optional skin surface of the patient's body by a high-frequency power source 24 connected to the terminal part 18 of the guide wire 10 and monitoring the magnitude of an impedance between the guide wire 10 and the counter electrode 23.

The whole of the implanted device 16 of the medical wire is projected out of a distal opening of the catheter 20 so as to locate the joint member 15 at the distal opening. When the distal end of the guide wire 10 is then situated at the distal opening of the catheter 20, the impedance by the high-frequency voltage for measurement greatly reduces rapidly, thereby detecting the fact that the implanted device 16 has been deposited properly in the patient's body.

In this stage, a monopolar high-frequency current for detaching the implanted device is applied between the guide wire 10 and the counter electrode 23 by the high-frequency power source 24.

As a result, the joint member 15 is heated at the distal end of the guide wire 10 with the high-frequency current with reaching a high temperature, whereby the joint member 15 is melted and severed. Therefore, the implanted device 16 is detached from the guide wire 10, whereby the implanted device 16 can be deposited in the cerebral aneurysm. The implanted device 16 returns to its original double-coiled form by its elasticity to serve as a thrombus-forming member.

The high-frequency current is preferably such that the frequency and power are about 100 to 5,000 kHz and about 0.1 to 20 W, respectively, because it does not adversely affect the patient's body.

The high-frequency voltage for measurement may be such that the frequency and voltage are about 100 to 5,000 kHz and about 0.1 to 3 V, respectively.

As described above, the monopolar high-frequency current is applied to the joint member 15 through the guide wire 10 utilizing the conductivity of the guide wire 10, thereby heating the joint member 15 with certainty. Therefore, there is no need for lead wires extending to the joint member 15, thereby providing high operability, and no possibility that the lead wires could break. Accordingly, even when the implanted device 16 is pulled back for the purpose of changing or correcting the position of the implanted device deposited once, such an operation can be easily performed with certainty, securing high reliability.

According to the above-described construction, the joint member 15 is composed of a rod of a swelling resin, the outer diameter of which increases by at least 10% when brought into contact with water. Therefore, the outer diameter of the joint member 15 can be increased by, for example, dipping it in a saline solution prior to implementation of the medical wire, so that sufficiently great joint strength can be provided between the coiled distal part 14 of the guide wire 10 and the joint member 15, and between the primary coil portion 16A of the implanted device 16 and the joint member 15.

Since the outer diameter of the joint member 15 increases by swelling, it undergoes neither bending nor deformation as understood from FIG. 3, whereby the pushing force applied to the guide wire 10 is reliably transmitted to the implanted device 16 through the joint member 15.

As a result, the implanted device 16 can be inserted while maintaining proper pose of connection without changing the connection state of the guide wire 10 with the implanted device 16 through the joint member 15. Therefore, the implanted device 16 can be reliably deposited at the intended site in the patient's body. In addition, the implanted device 16 can also be pulled back surely by pulling back the guide wire 10 as needed.

Since the outer diameter d1 of the swollen joint member 15 becomes greater than the outer diameter d2 of the coiled distal part 14 of the guide wire 10 and the outer diameter d3 of the primary coil portion 16A of the implanted device 16, the guide wire 10 and the implanted device 16 are reliably prevented from coming into contact with each other upon moving along within the catheter 20 as apparent from FIG. 3. Accordingly, the joint member 15 is surely melted and severed by application of the high-frequency current.

Furthermore, since the outer diameter of the unswollen joint member 15 is as small as 0.10 to 0.35 mm, it can be easily connected to the guide wire 10 and implanted device 16, if they are those to be used generally.

When the state that the implanted device is properly deposited is detected by the impedance reduction detecting method, the barrier formed by the joint member 15 surely prevents the implanted device 16 from coming into direct contact with the distal end of the guide wire 10 within the catheter because the outer diameter of the joint member 15 increases by swelling as described above. Therefore, the impedance reducing phenomenon surely occurs when the distal end of the guide wire 10 is exposed out of the catheter, whereby the state that the implanted device has been deposited properly at the intended site in the patient's body can be detected with high reliability, while preventing wrong detection.

Moreover, since a clearance L between the distal end of the coiled distal part 14 of the guide wire 10 and the proximal end of the primary coil portion 16A of the implanted device 16 connected through the joint member 15, is determined in a range of from 0.3 to 5.0 mm, the joint member 15 can be surely melted and severed without leaving a great residue with a high-frequency current of a frequency of about 100 to 5,000 kHz and power of about 0.1 to 20 W.

As a result, the joint member 15 can be surely melted and severed by applying a high-frequency current for an extremely short period of within 1 to 3 seconds, for example. Therefore, stress imposed not only on a surgeon, but also on the patient can be greatly lightened. In addition, there is no possibility of forming metal ions as like in an electrolytic method, thus alleviating greatly the possibility that any contingencies may occur in the patient's body during the depositing operation.

Figure 6:
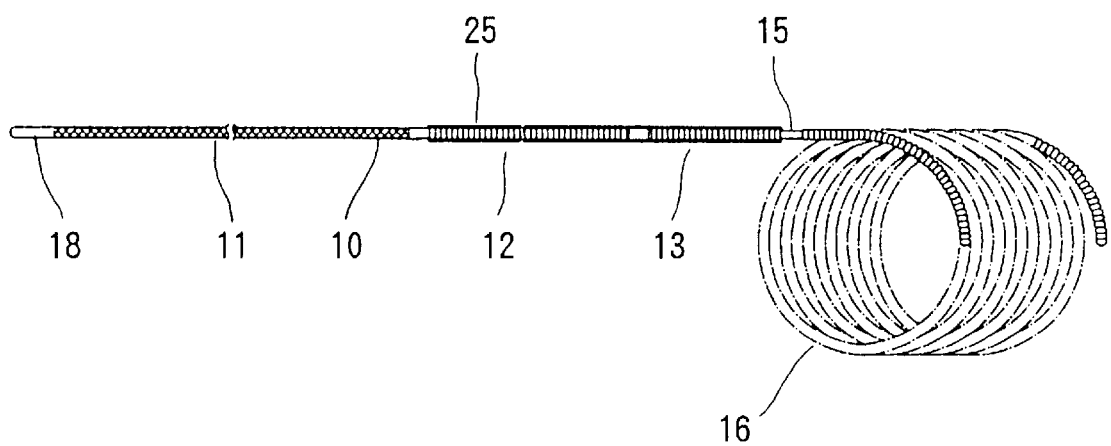
FIG. 6 illustrates a construction of a medical wire which is another embodiment of the present invention.

FIG. 6 illustrates another embodiment of the present invention. In this embodiment, an electrically insulated coating 25 is provided on the peripheral surfaces of the flexible part 12 and distal X-ray impervious part 13 in the guide wire 10. This electrically insulated coating 25 can be formed by one of various polymers, for example, polyurethane, polyethylene, polypropylene, silicone resins and polyamide resins such as nylon. A hydrophilic polymer coat may be further provided on the coating of this resin.

According to the medical wire of such a construction, the implanted device 16 can be detached and deposited by applying a monopolar high-frequency current through the guide wire 10 as like in the above-described embodiment. In addition, since almost the entire surface of the guide wire 10, with which the body tissue is brought into contact, is covered with the electrically insulated coating 25, the medical wire may be inserted into the patient's body without using any catheter.

The present invention will hereinafter be described more specifically by the following experimental example. However, the present invention is not limited to or by this example.

EXPERIMENTAL EXAMPLE

The following respective members or devices were provided.

(1) Guide wire

A stainless steel wire having a diameter of 0.4 mm at its proximal part and an overall length of 1,800 mm with its distal part tapered over 400 mm, produced by closely winding a wire having a diameter of 0.08 mm on the peripheral surface of a tapered core wire having a diameter of 0.05 mm.

(2) Joint member

A columnar rod having a diameter of 0.20 mm and a length of 10 mm composed of a swelling vinyl alcohol copolymer having a polymerization degree of about 2,000 and a saponification degree of 98% or higher.

(3) Implanted device

A double-coiled wire constructed of a platinum alloy wire having a diameter of 0.05 mm, and having a primary coil diameter of 0.4 mm and a secondary coil diameter of 3 to 12 mm.

Using the above members or devices and following the construction of FIG. 1, a medical wire according to the present invention was produced by inserting a proximal part 15A of the joint member 15 into the coiled distal part 14 of the guide wire 10, which had an outer diameter of 0.4 mm and had been formed of only the wire to bond them with an adhesive, and inserting a distal part 15B of the joint member 15 into a proximal portion of the implanted device 16 to bond them with an adhesive, thereby connecting the implanted device 16 to the guide wire 10 through the joint member 15.

In this medical wire, the clearance L between the distal end of the coiled distal part 14 and the proximal end of the implanted device 16 was about 0.7 mm.

The joint member 15 of this medical wire swelled and increased its outer diameter to about 0.5 mm when dipped for 3 minutes in physiological saline. This increment rate was about 150%, and its breaking strength in the swollen state was about 150 g.

A catheter having an inner diameter of about 0.5 mm and an outer diameter of about 1 mm was arranged through a blood vessel from a femoral artery so that the distal end thereof was situated at a cerebral aneurysm. The medical wire as above was then inserted through the catheter. Applied to the guide wire 10 was high-frequency voltage for measurement of a frequency of 300 kHz and voltage of 1 V by a high-frequency power source connected to the terminal part 18 situated at the proximal end of the guide wire 10. An impedance reducing phenomenon was detected at the time the distal end of the guide wire 10 was situated at the distal opening of the catheter. Specifically, the impedance between the proximal end of the guide wire 10 and a counter electrode 23 for body earth, which was about 2 kω during the inserting operation, rapidly reduced to about 300 ω.

In the above state, a high-frequency current of a frequency of 300 kHz and power of about 5–6 W was applied to the guide wire 10 by the high-frequency power source connected to the guide wire 10. As a result, it was confirmed that the joint member 15 was instantaneously melted and severed to detach the implanted device 16 from the guide wire 10, whereby the implanted device 16 was deposited in the cerebral aneurysm.

Although the embodiments of the present invention have been described above, various modifications and variations may be made to the present invention. For example, the guide wire 10 may be composed of a single wire or a bundle of wires, or may be a wire composed of multiple wire segments of suitable lengths connected in series.

In the present invention, various kinds of implanted devices 16 may be employed. Specifically, thrombus-forming members in the form of a coil piece or forms other than the coil piece, such as capsules containing a drug therein, which are left in the patient's body to gradually release the drug, embolizing members for occluding tubular organs, such as balloons, as well as suitable devices which perform a medical function or medically auxiliary function while implanted.

According to the medical wire of the above-described construction, the joint member through which the implanted device is connected to the guide wire is composed of a rod of a resin having specific swelling characteristics. Therefore, the joint strength of the joint member with the guide wire and the implanted device can be made sufficiently great utilizing the swelling of the joint member to increase its outer diameter by absorbing water upon bring the joint member into contact with, for example, physiological saline before insertion into a patient's body, or upon coming into contact with blood or other humors in the course of insertion into the patient's body. In particular, when joints of the guide wire and implanted device with the joint member are in the form of a coil, sufficiently great joint strength can be surely obtained by inserting both end parts of the joint member into the respective coils to connect them.

In addition, since the outer diameter of the joint member increases by swelling, the joint member undergoes neither bending nor deformation, and moreover the pushing force applied to the guide wire is reliably transmitted to the implanted device through the joint member.

As a result, the implanted device can be inserted while maintaining proper pose of connection without changing the connection state of the guide wire with the implanted device through the joint member. Therefore, the implanted device can be reliably deposited at the intended site in the patient's body and also pulled back surely.

Furthermore, the joint member of the medical wire implemented for the patient's body swells to contain a moderate amount of water, and hence can be successfully melted and severed by applying a high-frequency current.

Moreover, since the outer diameter of the joint member increases by swelling, the electrical insulation between the guide wire and the implanted device can be suitably ensured, both guide wire and implanted device can be reliably prevented from coming into contact with each other during use, and the implanted device can be surely detached from the guide wire by applying a high-frequency current to the joint member.

According to the method of the present invention, the use of such a medical wire as described above prevents direct contact of the implanted device with the guide wire, which causes an incorrect detection. Therefore, the state that the implanted device is deposited properly in a patient's body can be detected with high reliability by the impedance reduction detecting method.

What is claimed is:

1. A medical wire having an implanted device, in which the implanted device is connected to a distal end of a conductive guide wire through a joint member, and the joint member is heated by applying a high-frequency current through the guide wire, whereby the joint member is melted and severed so as to detach the implanted device from the guide wire, wherein the joint member is composed of a rod of a swelling resin, the outer diameter of which increases by at least 10% when brought into contact with water.

2. The medical wire according to claim 1, wherein the joint member is connected to the guide wire by inserting its proximal part into a coiled distal part of the guide wire and connected to the implanted device by inserting its distal part into a coil portion forming the implanted device.

3. The medical wire according to claim 2, wherein the outer diameter of the joint member in a swollen state is greater than any of the outer diameters of the coiled distal part of the guide wire and the coil portion forming the implanted device.

4. The medical wire according to claim 1, wherein the joint member has an outer diameter of 0.10 to 0.35 mm in an unswollen state.

5. The medical wire according to claim 4, wherein the joint member has an outer diameter of 0.25 to 1.00 mm in a swollen state.

6. The medical wire according to claim 1, wherein the joint member has breaking strength of at least 100 g in a swollen state.

7. The medical wire according to claim 1, wherein the joint member is made of poly(vinyl alcohol) or a vinyl alcohol copolymer.

8. The medical wire according to claim 1, wherein a clearance between the distal end of the guide wire and the proximal end of the implanted device connected through the joint member to the guide wire, is 0.3 to 5.0 mm.

9. The medical wire according to claim 1, wherein the joint member is melted and severed by applying a high-frequency current of a frequency of 100 to 5,000 kHz and power of 0.1 to 20 W between the guide wire and a counter electrode.

10. A method for using a medical wire through a catheter arranged in a patient's body, said medical wire having an implanted device, in which the implanted device is connected to a distal end of a conductive guide wire through a joint member, and the joint member is heated by applying a high-frequency current through the guide wire, whereby the joint member is melted and severed so as to detach the implanted device from the guide wire, wherein the joint member is composed of a rod of a swelling resin, the outer diameter of which increases by at least 10% when brought into contact with water;

the method comprises dipping the joint member in a saline solution before insertion into the patient's body.

11. A method for using a medical wire through a catheter arranged in a patient's body, said medical wire having an implanted device, in which the implanted device is connected to a distal end of a conductive guide wire through a joint member, and the joint member is heated by applying a high-frequency current through the guide wire, whereby the joint member is melted and severed so as to detach the implanted device from the guide wire, wherein the joint member is composed of a rod of a swelling resin, the outer diameter of which increases by at least 10% when brought into contact with water;

the method comprises inserting the guide wire into the catheter in a state that high-frequency voltage for measurement is applied between the guide wire and a counter electrode provided on the patient's body, and detecting an impedance reducing phenomenon that an impedance between the guide wire and the counter electrode reduces rapidly, thereby confirming that the implanted device has been deposited properly in the patient's body.

* * * * *